(12) United States Patent
Harrold

(10) Patent No.: US 6,419,663 B2
(45) Date of Patent: Jul. 16, 2002

(54) MECHANICALLY PROPELLED, METERED LIQUID DISPENSER

(76) Inventor: John E. Harrold, 27 Milford Rd., Bloomsbury, NJ (US) 08804

(*) Notice: Subject to any disclaimer, the term of this patent is extended or adjusted under 35 U.S.C. 154(b) by 0 days.

(21) Appl. No.: 09/865,076

(22) Filed: May 24, 2001

Related U.S. Application Data

(63) Continuation-in-part of application No. 09/574,191, filed on May 18, 2000.

(51) Int. Cl.$^7$ ............................................. A61M 35/00
(52) U.S. Cl. ..................................................... 604/298
(58) Field of Search ................................ 604/152, 131, 604/134–136, 298, 294, 245–249, 207–200, 228

(56) References Cited

U.S. PATENT DOCUMENTS

| | | | |
|---|---|---|---|
| 3,934,585 A | * 1/1976 | Maurice | 128/225 |
| 5,267,986 A | 12/1993 | Py | 604/294 |
| 5,401,259 A | 3/1995 | Py | 604/294 |
| 5,613,957 A | 3/1997 | Py | 604/294 |
| 5,685,869 A | 11/1997 | Py | 604/294 |

* cited by examiner

Primary Examiner—Anhtuan T. Nguyen
Assistant Examiner—Ann Y. Lam
(74) Attorney, Agent, or Firm—Kenneth P. Glynn, Esq.

(57) ABSTRACT

The present invention mechanically propelled, liquid metered dispenser includes a main housing with liquid storage and a liquid advancing component for either allowing liquid to flow out or assisting in the flow of liquid out of the main housing by exerting pressure, into a metered dosage dispensing chamber in response to a loading movement of a cocking mechanism. The chamber has an inlet connected to the main housing with a one-way valve to only permit flow of liquid into the chamber. The chamber also has an outlet orifice for dispensing liquid therefrom in a metered amount. The chamber has a reciprocal plunger and has a load and release component connected to it, which includes a cocking mechanism, a locking mechanism, and a spring. The cocking mechanism is functionally connected to the plunger so as to move in harmony therewith, or, more preferably, to move a relatively short distance relative to the distance traveled by the cocking mechanism.

16 Claims, 2 Drawing Sheets

MECHANICALLY PROPELLED, METERED LIQUID DISPENSER

REFERENCES TO RELATED APPLICATIONS

This patent application is a continuation-in-part of copending U.S. patent application Ser. No. 09/574,191, filed by the same inventor herein on May 18, 2000, entitled "Metered, Mechanically Propelled, Liquid Dispenser".

BACKGROUND OF THE INVENTION

1. Field of the Invention

The present invention relates to mechanically propelled metered dispensers which are plunger-activated by a cocking mechanism and dispense a liquid stream or a mist of liquid dispensing material, e.g., medication. The present invention dispensers include provision for automatic advancement of a liquid in a metered amount into the dispensing chamber in response to pulling the cocking mechanism to the cocked (loaded) position.

2. Information Disclosure Statement

The following patents are representative of metered, mechanically propelled, liquid dispensers:

U.S. Pat. No. 3,934,585 to David M. Maurice discloses a method and apparatus for applying therapeutic eye drops to the eye by metering a predetermined volume of fluid and rapidly applying a pressure to one end of the metered fluid for forcing the fluid from a nozzle of means defining a small passageway such as and open-ended tube as a droplet having sufficient velocity to travel a generally horizontal distance in space to the eye. Unit dose application and multiple dose applications are included and provision is made for preventing anticipatory blinking of the eye during self-administration.

U.S. Pat. No. 5,267,986 describes and illustrates a cartridge for actuating a piston-like or accordion-like dispenser-vial for applying medication to any eye. The cartridge includes a housing for holding the dispenser-vial and a telescoping cylinder for compressing the dispenser-vial in the longitudinal direction to actuate the vial. The cartridge includes a locking mechanism for locking the telescoping cylinder to restrict its movement and a trigger mechanism for releasing the cylinder from the locked position so that a drop is released from the dispenser. The housing includes a finger for engaging the lower eyelid and exposing the conjunctival cul de sac.

U.S. Pat. No. 5,401,259 discloses a cartridge for actuating a piston-like or accordion-like dispenser-vial for applying medicament to the eye. The cartridge includes a housing for holding the dispenser-vial and a telescoping cylinder for compressing the dispenser-vial in the longitudinal direction to activate the vial. The cartridge includes a locking mechanism for locking the telescoping cylinder to restrict its movement and a lever mechanism for releasing the cylinder form the locked position so that a drop is released from the dispenser. The housing includes a finger for engaging the lower eyelid and exposing the conjunctival cul-de-sac.

U.S. Pat. No. 5,613,957 to Daniel Py discloses an apparatus used for applying medicament to an eye and to store the medicament in a medicament chamber. A nozzle is coupled in fluid communication with the medicament chamber and is formed by an outer nozzle portion and an nozzle portion. A tight interface is defined between the inner nozzle portion and the outer nozzle portion and is normally in a closed position to prevent the passage of medicament through the nozzle. The interface opens in response to the flow of medicament of sufficient pressure into it to permit the passage of medicament through the nozzle for release into the eye.

U.S. Pat. No. 5,685,869 to Daniel Py describes and illustrates an apparatus used to apply medicament to an eye and to store the medicament in the medicament chamber. A nozzle is coupled in fluid communication with the medicament chamber and is formed by an outer nozzle portion and an inner nozzle portion received within the outer nozzle portion. A seam is formed by the interface of the inner nozzle portion and the outer nozzle portion and is normally in a closed position to prevent the passage of medicament through the nozzle. The seam opens in response to the flow of medicament or sufficient pressure into the seam to permit the passage of medicament through the nozzle for release into the eye.

Notwithstanding the prior art, the present invention is neither taught nor rendered obvious thereby.

SUMMARY OF THE INVENTION

The present invention is directed to a mechanically propelled, liquid metered dispenser for dispensing liquids such as medications in predetermined dosages. The dispenser includes a main housing having liquid storage means, i.e. the main housing either is adapted to itself hold liquid therein or is adapted to receive and hold a component which itself will hold and store a liquid, e.g., a pouch or container. The main housing is also adapted to contain a liquid advancing means for either allowing liquid to flow out or assisting in the flow of liquid out of the main housing by exerting pressure. Thus, the liquid advancing means in the main housing is adapted to automatically advance liquid from the main housing to a metered dosage dispensing chamber in response to a loading movement of a cocking mechanism. The metered dosage dispensing chamber has an inlet connected to the main housing and has a one-way valve in the inlet to permit flow of liquid from the main housing liquid storage means to the metered dosage dispensing chamber and to prevent flow of liquid from the metered dosage dispensing chamber to said the storage means. The metered dosage dispensing chamber also has an outlet orifice for dispensing liquid therefrom in a metered amount.

The metered dosage dispensing chamber is adapted to contain a reciprocal plunger means and has a load and release means connected to it. This load and release component includes a cocking mechanism, a locking mechanism, a spring, and a plunger. The cocking mechanism is functionally connected to the plunger so as to move in harmony therewith, or, more preferably, to move a relatively short distance relative to the distance traveled by the cocking mechanism. This preferred embodiment includes the plunger and cocking mechanism connected in a slidable, non-removable manner with a predetermined, permittable distance of travel between the plunger and the cocking mechanism. The plunger is connected to and at least partially contained within the metered liquid dispensing chamber. The main spring is connected to the cocking mechanism to bias it to a first position, being a rest position toward the metered liquid dispensing chamber.

The locking mechanism is connected to the cocking mechanism to lock it in a second position, being a stressed position away from the liquid metered dispensing chamber, wherein, when the cocking mechanism is pulled away from the chamber, the locking mechanism locks the cocking mechanism in the second position, draws the plunger at least partially out of the open area of the chamber and permits flow of liquid from the liquid storage means to said chamber, and wherein, when the aforesaid locking mechanism is released, the spring biases the cocking mechanism and the plunger toward said chamber and dispenses a metered amount of liquid from the chamber.

In some preferred embodiments, the liquid advancing means is selected from the group consisting of a pressurized container, a piston-driven chamber, a collapsible pouch and a bellows-type chamber. Usually, the liquid advancing means is under a pressure insufficient to overcome said spring. In other words, the liquid advancing means does not exert sufficient force to push liquid into the chamber and to move back the plunger and cocking mechanism to cause liquid to flow into the chamber when it is not intentionally drawn into the chamber by a user pulling on the cocking mechanism.

In other preferred embodiments, the outlet orifice includes a one-way valve which is spring-loaded and permits liquid to exit the chamber and prevents air from entering chamber. In these embodiments, the liquid advancing means exerts a pressure toward the chamber which is insufficient to overcome spring and is also insufficient to overcome the spring-loaded one way valve of the outlet orifice to prevent undesirable seeping.

The present invention dispenser preferably includes a plunger stop located between the metered dosage dispensing chamber and the cocking mechanism to set a predetermined distance of travel of the plunger within the chamber.

BRIEF DESCRIPTION OF THE DRAWINGS

The present invention should be more fully understood when the specification herein is taken in conjunction with the drawings appended hereto wherein.

DETAILED DESCRIPTION OF THE PRESENT INVENTION

Figure 1:
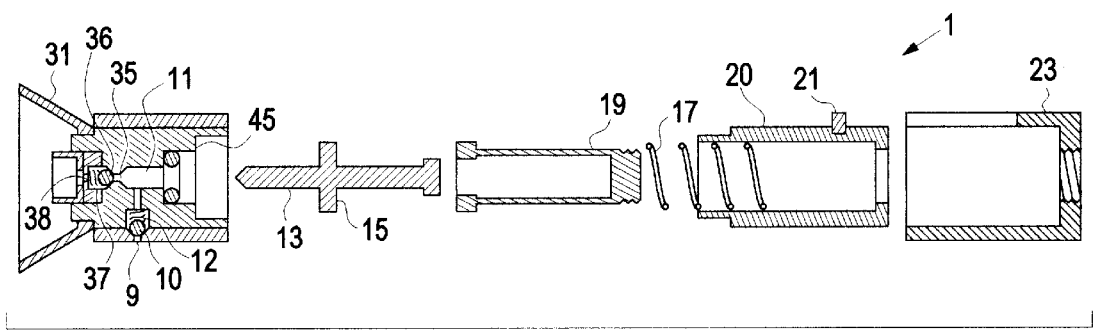
FIGS. 1, 2, 3, and 4, show a blown apart side cut view of a top portion, a front view, a side partially cut view in a release and dispense form, and a side partially cut view of a top portion in an open chamber locked cocking mechanism form, respectively, of a preferred embodiment of a present invention dispenser.
Figure 2:
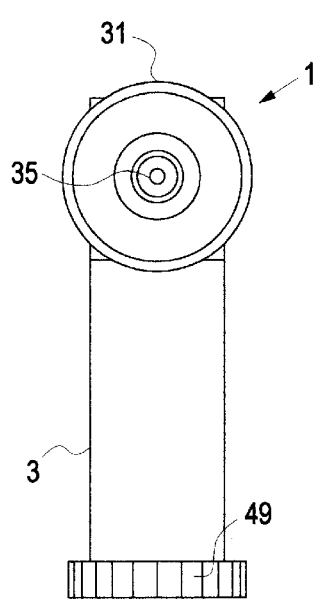

The present invention relates to mechanically propelled, metered liquid dispensers. The present invention dispenser has a plunger activated by a cocking mechanism, which is loaded and subsequently released for propelling liquid through a dispensing orifice. The liquid may be dispensed in the form of a liquid stream or a fine mist.

There is a liquid advancing means which automatically advances the liquid in a main housing into a metered dosage dispensing chamber. The liquid from the metered dosage dispensing chamber is dispensed through a dispensing orifice, once the cocking mechanism is unlocked and, thus fired.

The dispensing orifice includes a one-way valve which allows the liquid in the form of a stream or fine mist to flow out of the dispensing orifice but prevents air from returning to the chamber. In this way, preservation-free liquids may be used without intake of contaminating air.

The present invention is intended primarily for the dispensing of liquid stream and fine spays or mists, e.g. to the eye. However, it could also be used for the dispensing of liquids and fine sprays to other body parts, as well as for the dispensing of antiseptics and the like to open wounds, and could be used for liquid and fine mist dispensing for any desired application.

Referring now to FIGS. 1, 2, 3, and 4, there is shown a blown apart side cut view of a top portion, a front view, a side partially cut view in a release and dispense form, and a side partially cut view of a top portion in an open chamber locked cocking mechanism form, respectively, of a preferred embodiment of a present invention mechanically propelled, metered liquid dispenser 1.

The device 1 includes a main housing 3 having storage means 4, in this case the space created by the main housing 3 and the piston 47. Liquid storage means 4 contains liquid 41 to be dispensed, as shown. There is a piston 47 which is advanced by spring 43, and a lid 49, as shown.

There is also a metered dosage dispensing chamber 11 for receiving a metered amount of the liquid 41, and load and release means for dispensing the liquid 41 in the metered dosage dispensing chamber 11 through a dispensing orifice. The load and release means or mechanism includes a plunger 13, a slider 19, a fixed barrel 20, a locking means 21, a spring 17 and a handle 23. The slider 19 and the handle 23 are screwed together to form a cocking mechanism.

The dispensing orifice includes a nozzle 35, a projection member 31 surrounding the nozzle 35, and a one-way valve 37, established by ball 36 and spring 38. The one-way valve 37 allows the liquid 41 to dispense through the nozzle 35 when a predetermined spring pressure is overcome, but prevents air from returning into the device 1.

The main housing 3 also includes an automatic liquid advancing means. In this case, the liquid advancing means is a piston 43 and spring 47 which advances liquid into chamber 11 when dispenser 1 is cocked. Other automatic liquid advancing means include pressurized containers, collapsible pouches with gravity feed, collapsible pouches with springs, spring or gravity-based automatically closing bellows, etc.

A connection means 9, in this case a tube, connects the main housing 3 with the metered dosage dispensing chamber 11. The connecting means 9 has a one-way valve, e.g. ball 10 and spring 12, which allows the liquid 41 to flow from the main housing 3 into the metered dosage dispensing chamber 11 when the metered dosage dispensing chamber 11 is open and the cocking mechanism is in a locked position, which is further defined hereinafter. The one-way valve prevents flow of liquid back into main housing 3.

The slider 19 and handle 23 (cocking mechanism) includes a locking capability and has a cocked position and a resting position. The locking means is a pin 21 on barrel 20, and the cocked position is achieved with pin 21 positioned in short slot 25 and the resting position means, with pin 21 in U-shaped slot 33. Other locking means and cocked and resting position arrangements include hood and loops, sliders with interlocking pieces, and the like.

The plunger 13 is movably fitted inside slider 19, as shown. The spring 17 is held in place by barrel 20 and exerts force against slider 19, as shown. The plunger 13 is adapted to partially fit into the metered dosage dispensing chamber 11, as shown. The flange 15 of plunger 13 acts as a strike for slider 19 to hit when released, and traverses a distance to where flange 15 hits stop 45 (FIGS. 1, 3, 4).

Figure 3:
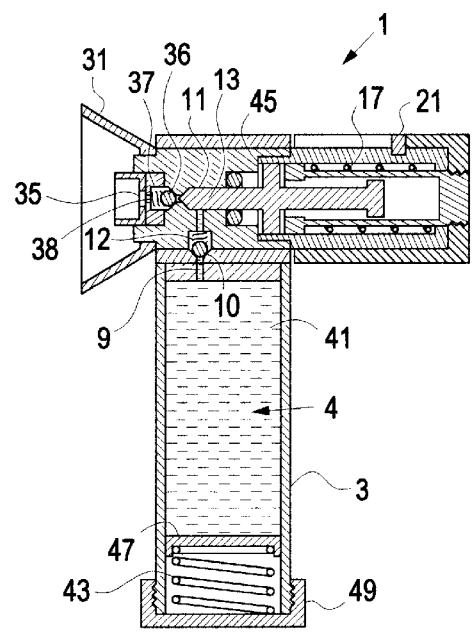
Figure 4:
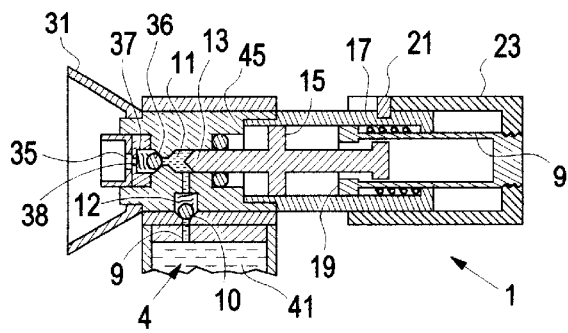

Referring now to FIGS. 3 and 4, there is shown the operation of the device 1. FIG. 3, shows the device 1 with the plunger 13 in its closed position, e.g. before loading (cocking) or after releasing (firing). FIG. 4 shows a top portion of the device 1 with the metered dosage dispensing chamber 11 filled and ready for firing.

In operation, when liquid 41 is advanced by cocking and automatic functioning of liquid advancing means 43, metered dosage dispensing chamber 11 is filled with a small amount of metered liquid 41. In order to dispense the liquid, plunger 13 is fired by slowly rotating the handle 23 of the cocking mechanism so that the locking means pin 21 is moved from the stressed position slot 25 to the rest position slot 33, thereby releasing the slider 19 and handle 23 to move toward the plunger 13 and then move plunger 13 through the chamber 11 to dispense liquid.

Figure 5:
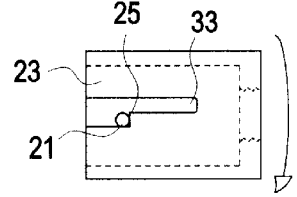
FIG. 5 shows the operation of the cocking mechanism of the present invention device of the preceding Figures in detail; and, FIGS. 6 and 7 show two alternative autodispensing arrangements of the present invention devices in side cut views.

FIG. 5 shows the operation of the cocking mechanism in more detail. In rotating the locking means pin 21 to the rest position slot 33, the slider 19 is forced by the spring 17 to push against the stop flange 15 on the plunger 13 so that the plunger 13 advances into the metered dosage dispensing chamber 11 and is stopped by metered dosage dispensing chamber stop 45, as shown in FIG. 3.

Because the firing distance from the slider 19 to the flange 15 is relatively large in comparison to the firing distance of the plunger 13 to the short distance to the metered dosage dispensing chamber stop 45, the liquid moves rapidly from the dispensing dosage dispensing chamber 11 through the dispensing nozzle. The dispensed liquid may be in the form of a fine mist or a liquid stream, depending upon nozzle size and design based on the liquid dispensed. Once the liquid 41 is dispensed, the cocking mechanism may be locked pulling back handle 23 and rotating it so that locking pin 21 is positioned in the loading slot 25, so that metered dosage dispensing chamber 11 is automatically refilled, and ready for the next dosage shot, as shown in FIG. 4.

Figure 6:
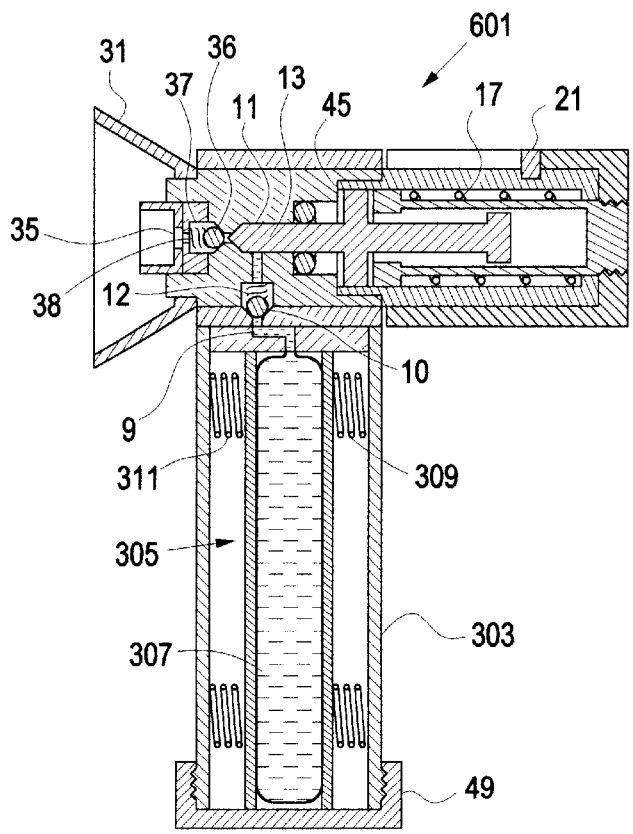
Figure 7:
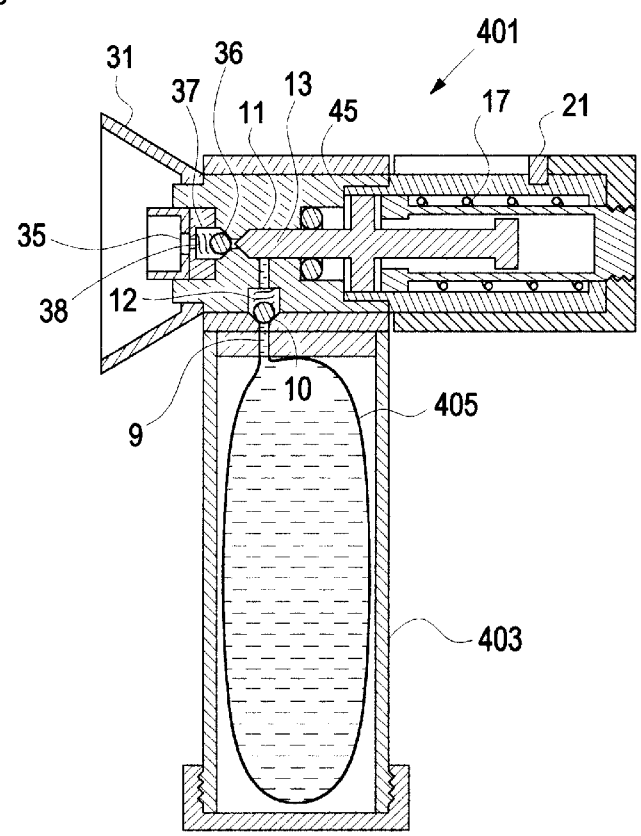

FIGS. 6 and 7 show two alternative autodispensing arrangements in side cut views. In both Figures, the components which are identical to those shown in FIG. 3 are identical, are thus identically numbered, and need not be rediscussed here as they also function identically to that shown in FIG. 3.

In FIG. 6, present invention device 601 includes main housing 303 with automatic dispensing means 305, in this case, a pouch 307, and springs 309 and 311, with squeeze plates 313 and 315. These plates are biased against pouch 307 and have enough pressure to move liquid from pouch 307 into chamber 11, but not enough pressure to overcome spring 38, so as to fill the chamber, but not force liquid out of the chamber. This is achieved with the load and release described in conjunction with FIGS. 2 through 5 above.

In FIG. 7, a collapsible bladder is shown as the autodispensing means. Here, device 401 includes a main housing 403 with a filled bladder 405, which automatically squeezes liquid int chamber 11 when the device is cocked. Firing is aceived as described above.

Obviously, numerous modifications and variations of the present invention are possible in light of the above teachings. It is therefore understood that within the scope of the appended claims, the invention may be practiced otherwise than as specifically described herein.

What is claimed is:

1. A mechanically propelled, liquid metered dispenser, which comprises:
   (a) a main housing having liquid storage means to contain liquid advancing means;
   (b) a liquid advancing means in said main housing, adapted to automatically advance liquid from said main housing to a metered dosage dispensing chamber in response to a loading movement of a cocking mechanism;
   (c) a metered dosage dispensing chamber having an inlet connected to said main housing and having a one-way valve within said inlet to permit flow of liquid from said main housing liquid storage means to said metered dosage dispensing chamber and to prevent flow of liquid from said metered dosage dispensing chamber to said liquid storage means, and said metered dosage dispensing chamber having an outlet orifice for dispensing liquid therefrom in a metered amount, said metered dosage dispensing chamber being adapted to contain a reciprocal plunger means;
   (d) a load and release means connected to said metered liquid dispensing chamber, said load and release means including a cocking mechanism, a locking mechanism, a spring, and a plunger, said cocking mechanism functionally connected to said plunger, said plunger being connected to said metered liquid dispensing chamber, said spring being connected to said cocking mechanism to bias it to a first position, being a rest position toward said metered liquid dispensing chamber, said locking mechanism being connected to said cocking mechanism to lock it in a second position, being a stressed position away from said liquid metered dispensing chamber, wherein, when said cocking mechanism is pulled away from said chamber, said locking mechanism locks said cocking mechanism in said second position, draws said plunger at least partially out of said chamber and permits flow of liquid from said liquid storage means to said chamber, and wherein, when said locking mechanism is released, said spring biases said cocking mechanism and said plunger toward said chamber and dispenses a metered amount of liquid from said chamber; and,
   (e) a plunger stop located between said metered dosage dispensing chamber and said cocking mechanism to set a predetermined distance of travel of said plunger within said chamber, wherein said predetermined distance of travel of said plunger in said chamber is less than a distance of travel of said cocking mechanism from said first position to said second position.

2. The dispenser of claim 1 wherein said liquid advancing means is selected from the group consisting of a pressurized container, a piston-driven chamber, a collapsible pouch, an expandable/contractable bladder and a bellows-type chamber.

3. The dispenser of claim 2 wherein said liquid advancing means is under a pressure insufficient to overcome said spring.

4. The dispenser of claim 1 wherein said outlet orifice includes a one-way valve which is spring-loaded and permits liquid to exit said chamber and prevents air from entering said chamber.

5. The dispenser of claim 4 wherein said liquid advancing means exerts a pressure toward said chamber which is insufficient to overcome said spring and insufficient to overcome said spring-loaded one way valve of said outlet orifice.

6. The dispenser of claim 5 wherein said liquid advancing means is selected from the group consisting of a pressurized container, a piston-type chamber, a collapsible pouch and a bellows-type chamber.

7. The dispenser of claim 1 wherein said inlet of said chamber is located at an approximately 90 degree angle relative to a direction of travel of said plunger.

8. The dispenser of claim 1 wherein said dispenser includes a fixed cocking housing attached to said metered liquid dispensing chamber, and wherein said cocking mechanism has one of a male and corresponding female locking component located thereon and said fixed cocking housing has the other of a male and corresponding female component located thereon.

9. A mechanically propelled, liquid metered dispenser, which comprises:
   (a) a main housing having liquid storage means for storing liquid therein, said main housing adapted to contain liquid advancing means;
   (b) a liquid advancing means in said main housing, adapted to automatically advance liquid from said main housing to a metered dosage dispensing chamber in response to a loading movement of a cocking mechanism;
   (c) a metered dosage dispensing chamber having an inlet connected to said main housing and having a one-way valve within said inlet to permit flow of liquid from said main housing liquid storage means to said metered dosage dispensing chamber and to prevent flow of liquid from said metered dosage dispensing chamber to said liquid storage means, and said metered dosage dispensing chamber having an outlet orifice for dispensing liquid therefrom in a metered amount, said metered dosage dispensing chamber being adapted to contain a reciprocal plunger means;
   (d) a load and release means connected to said metered liquid dispensing chamber, said load and release means including a cocking mechanism, a locking mechanism, a spring, and a plunger, said cocking mechanism functionally connected to said plunger in a slidable, non-removable manner with a predetermined, permittable distance of travel between said plunger and said cocking mechanism, said plunger being connected to said metered liquid dispensing chamber, said spring being connected to said cocking mechanism to bias it to a first position, being a rest position toward said metered liquid dispensing chamber, said locking mechanism being connected to said cocking mechanism to lock it in a second position, being a stressed position away from said liquid metered dispensing chamber, wherein, when said cocking mechanism is pulled away from said chamber, said locking mechanism locks said cocking mechanism in said second position, draws said plunger at least partially out of said chamber and permits flow of liquid from said liquid storage means to said chamber, and wherein, when said locking mechanism is released, said spring biases said cocking mechanism and said plunger toward said chamber and dispenses a metered amount of liquid from said chamber; and,
   (e) a plunger stop located between said metered dosage dispensing chamber and said cocking mechanism to set a predetermined distance of travel of said plunger within said chamber, wherein said predetermined distance of travel of said plunger in said chamber is less than a distance of travel of said cocking mechanism from said first position to said second position.

10. The dispenser of claim 9 wherein said liquid advancing means is selected from the group consisting of a pressurized container, a piston-driven chamber, a collapsible pouch, an expandable/contractable bladder and a bellows-type chamber.

11. The dispenser of claim 10 wherein said liquid advancing means is under a pressure insufficient to overcome said spring.

12. The dispenser of claim 9 wherein said outlet orifice includes a one-way valve which is spring-loaded and permits liquid to exit said chamber and prevents air from entering said chamber.

13. The dispenser of claim 12 wherein said liquid advancing means exerts a pressure toward said chamber which is insufficient to overcome said spring and insufficient to overcome said spring-loaded one way valve of said outlet orifice.

14. The dispenser of claim 13 wherein said liquid advancing means is selected from the group consisting of a pressurized container, a piston-type chamber, a collapsible pouch and a bellows-type chamber.

15. The dispenser of claim 9 wherein said inlet of said chamber is located at an approximately 90 degree angle relative to a direction of travel of said plunger.

16. The dispenser of claim 9 wherein said dispenser includes a fixed cocking housing attached to said metered liquid dispensing chamber, and wherein said cocking mechanism has one of a male and corresponding female locking component located thereon and said fixed cocking housing has the other of a male and corresponding female component located thereon.

* * * * *